(12) United States Patent
Lang et al.

(10) Patent No.: US 10,933,126 B2
(45) Date of Patent: Mar. 2, 2021

(54) CLOSTRIDIUM DIFFICILE IMMUNOGENIC COMPOSITIONS AND METHODS OF USE

(71) Applicant: The Board of Regents of the University of Oklahoma, Norman, OK (US)

(72) Inventors: Mark L. Lang, Edmond, OK (US); Jimmy D. Ballard, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 16/401,308

(22) Filed: May 2, 2019

(65) Prior Publication Data

US 2019/0336593 A1 Nov. 7, 2019

Related U.S. Application Data

(60) Provisional application No. 62/666,270, filed on May 3, 2018.

(51) Int. Cl.
| | |
|---|---|
| *A61K 39/00* | (2006.01) |
| *A61K 39/02* | (2006.01) |
| *A61K 39/08* | (2006.01) |
| *A61P 31/04* | (2006.01) |
| *A61P 37/04* | (2006.01) |
| *A61P 1/00* | (2006.01) |

(52) U.S. Cl.
CPC ............. *A61K 39/08* (2013.01); *A61P 1/00* (2018.01); *A61P 31/04* (2018.01); *A61P 37/04* (2018.01); *A61K 2039/55505* (2013.01)

(58) Field of Classification Search
CPC ......... A61K 39/00; A61K 39/02; A61K 39/08
USPC .......... 424/184.1, 234.1, 247.1, 278.1, 282.1
See application file for complete search history.

(56) References Cited

U.S. PATENT DOCUMENTS

| | | | |
|---|---|---|---|
| 5,936,076 A | 8/1999 | Higa et al. | |
| 6,531,453 B1 | 3/2003 | Taniguchi et al. | |
| 7,226,597 B2 | 6/2007 | Ballard et al. | |
| 8,334,408 B2 | 12/2012 | Cerundolo et al. | |
| 8,597,663 B2 | 12/2013 | Monteiro et al. | |
| 9,220,681 B2 * | 12/2015 | Coulter ............. | A61K 39/0258 |
| 9,388,394 B2 | 7/2016 | Heinrichs et al. | |
| 9,669,083 B2 | 6/2017 | Castado | |
| 9,694,063 B2 | 7/2017 | Scarselli et al. | |
| 9,694,064 B2 | 7/2017 | Boutriau et al. | |
| 9,925,257 B2 | 3/2018 | Campos-Neto et al. | |
| 9,926,345 B2 | 3/2018 | Melnyk et al. | |
| 2003/0157135 A1 | 8/2003 | Tsuji et al. | |
| 2004/0242499 A1 | 12/2004 | Uematsu et al. | |
| 2008/0317769 A1* | 12/2008 | Kang ..................... | A61K 39/39 424/184.1 |
| 2012/0269857 A1 | 10/2012 | Cerundolo et al. | |
| 2013/0315959 A1* | 11/2013 | Costantino ............. | A61K 39/08 424/247.1 |
| 2016/0074496 A1 | 3/2016 | Lanis et al. | |

OTHER PUBLICATIONS

Lang, Mark L. et al.; "NKTfh cells stimulate IgG1 class switch against polysaccharide antigens"; Department of Microbiology and Immunology University of Oklahoma Health Sciences Center; May 14, 2017; 1 page.

Bertolo, Lisa et al.; "*Clostridium difficile* carbohydrates: glucan in spores, PSII common antigen in cells, immunogenicity of PSII in swine and synthesis of a dual *C. difficile*-ETEC conjugate vaccine"; Carbohydrate Research 354; 2012; pp. 79-86.

Adamo, Robert et al.; "Phosphorylation of the Synthetic Hexasaccharide Repeating Unit Is Essential for the Induction of Antibodies to *Clostridium difficile* PSII Cell Wall Polysaccharide"; ACS Chemical Biology 7; 2012; pp. 1420-1428.

Chu, Michele et al.; "A *Clostridium difficile* Cell Wall Glycopolymer Locus Influences Bacterial Shape, Polysaccharide Production and Virulence"; PLOS Pathogens; Oct. 14, 2016; 29 pages.

Monteiro, Mario A.; "The Design of a *Clostridium difficile* Carbohydrate-Based Vaccine"; *Clostridium difficile* Polysaccharide Vaccine; Chapter 21; 2016; pp. 397-408.

Romano, Maria R. et al.; "Recombinant *Clostridium difficile* Toxin Fragments as Carrier Protein for PSII Surface Polysaccharide Preserve Their Neutralizing Activity"; Toxins; vol. 6; 2014; pp. 1385-1396.

Jiao, Yuening et al.; "*Clostridium difficile* PSI polysaccharide: synthesis of pentasaccharide repeating block, conjugation to exotoxin B subunit, and detection of natural anti-PSI IgG antibodies in horse serum"; Carbohydrate Research 378; 2013; pp. 15-25.

Venkataswamy, Manjunatha M. et al.; "Lipid and glycolipid antigens of CD1d-restricted natural killer T cells"; Seminars in Immunology 22; 2010; pp. 68-78.

Devera, T. Scott et al.; "Memory B Cells Encode Neutralizing Antibody Specific for Toxin B from the *Clostridium difficile* Strains VPI 10463 and NAP1/BI/027 but with Superior Neutralization of VIP 10463 Toxin B"; American Society for Microbiology; Infection and Immunity; vol. 84 No. 1; Jan. 2016; pp. 194-204.

Rampuria, Pragya et al.; "Coordination between T helper cells, iNKT cells, and their follicular helper subsets in the humoral immune response against *Clostridium difficile* toxin B"; Journal of Leukocyte Biology; vol. 101; Feb. 2017; pp. 567-576.

Lang, Mark L. et al.; "Contribution of NKT follicular helper cells to T-dependent and T-independent humoral immunity against bacterial toxins and polysaccharides"; The Journal of Immunology; Jun. 13, 2017; pp. 1-3.

* cited by examiner

*Primary Examiner* — Rodney P Swartz
(74) *Attorney, Agent, or Firm* — Winstead PC

(57) ABSTRACT

An immunogenic composition containing a *Clostridium difficile* (*C. difficile*) surface polysaccharide II (PSII) or an immunogenic portion thereof; and an α-galactosylceramide (α-GC) or analog or derivative thereof, which is able to bind to a CD1d glycoprotein, optionally containing a *C. difficile* TcdB C-terminal domain (CTD), or an immunogenic portion thereof, and/or an adjuvant. A method of treating, ameliorating, or inhibiting a *C. difficile* infection or a *C. difficile*-associated diarrhea in a subject by administering the immunogenic composition, particularly in subjects at risk for a *C. difficile* infection. A method of protecting a subject's gut microflora by administering the immunogenic composition or a composition containing α-GC and an alum adjuvant.

12 Claims, 7 Drawing Sheets

CLOSTRIDIUM DIFFICILE IMMUNOGENIC COMPOSITIONS AND METHODS OF USE

CROSS REFERENCE TO RELATED APPLICATIONS

This application claims benefit under 35 U.S.C. 119(e) of U.S. Provisional Application Ser. No. 62/666,270, filed May 3, 2018, which is hereby expressly incorporated herein by reference in its entirety.

GOVERNMENT SUPPORT

This invention was made with government support under Grant Numbers AI125708 and AI134719 granted by the National Institutes of Health. The government has certain rights in the invention.

BACKGROUND

*Clostridium difficile* (*C. difficile*), a Gram-positive bacterium, also known in the art as *Clostridioides difficle*, is the leading cause of antibiotic-associated diarrhea and pseudomembranous colitis. The frequency and severity of outbreaks associated with *C. difficile* infection (CDI) has increased in recent years. The decreased levels of normal microflora in the intestines due to medical treatments such as antibiotic use and chemotherapy, can allow *C. difficile* to colonize and proliferate. In humans, *C. difficile*-associated disease (CDAD) is the most commonly diagnosed cause of hospital-associated and antimicrobial-associated diarrhea. The risk of CDAD has traditionally been higher among elderly patients and those that have undergone hospitalization, gastrointestinal surgery, are immunodeficient, or were exposed to antibiotics. Moreover, severe cases are being more frequently identified in younger patients and those without traditional risk factors. A steep rise in CDI incidents over the past decade is attributed to the emergence of the hypervirulent, and now prevalent strain ribotype 027 (also known as North American pulsotype 1 (NAP1) and BI), causing epidemic outbreaks with increased morbidity, mortality and high relapse rates.

Prevention of *C. difficile* is based on patient isolation, improved sanitation, improved infection control and antimicrobial restriction, all of which are associated with high healthcare costs. In addition, prophylactic use of antibiotics has been used for the prevention of infection; however, it led to an increase in the incidence of disease. Treatment of *C. difficile* infections is also problematic since the response to metronidazole, the main first-line treatment, is becoming unpredictable. Vancomycin, the alternative choice, is expensive and its use raises concern about emergence of vancomycin-resistant enterococci and other vancomycin-resistant organisms.

CDAD is also an important problem in many animal species, including horses and pigs. There is concern that *C. difficile* may be transmissible from animals to humans because the types of *C. difficile* isolated from animals are often the same as those found in people, including the outbreak strain ribotype 027. This concern has increased based on the finding of *C. difficile* in retail meat samples. The reported increasing incidence of CDAD, its recurrence rates, and its impact on morbidity and mortality, as well as the costs associated with treatment and appropriate isolation procedures to limit its spread make clear the need for effective prevention approaches of CDAD. Thus, there is a growing need to develop treatment modalities, including vaccines, for preventing and treating *C. difficile* infections in humans and animals to prevent CDAD or prevent recurrence. Additionally, vaccination is needed in animals to prevent animal disease and to reduce shedding of *C. difficile* so as to reduce the risk of zoonotic transmission.

The systemic pathology associated with fulminant CDAD is largely attributable to two secreted toxins known as Toxin A (TcdA) and Toxin B (TcdB), with the latter playing the dominant role in vivo. Recurrent infection is a particular problem in CDAD and is associated with progressive toxicity, and ultimately death. Therefore, stimulating protective toxin-specific immune memory is a current focus of efforts to generate a first generation vaccine. TcdA and TcdB cause extensive tissue damage and ultimately lead to human disease. Our work has focused on understanding how variations in the toxins produced by historical and epidemic strains change the extent of *C. difficile* virulence. Of particular interest are the differences in the sequence and activities of TcdB, which has been implicated as a critical *C. difficile* virulence factor.

TcdB is a single chain polypeptide toxin where the glucosyltransferase domain (GTD) is located at the N-terminus (amino acids 1-543), followed by an autoprocessing site between amino acid 543 and 544 which is subject to intramolecular cleavage by the cysteine protease domain (CPD) located in amino acids 544-807, a hydrophobic transmembrane domain (TMD) located in amino acids 956-1128, and a putative receptor binding domain at the C-terminus (CTD) located in amino acids 1651-2366. The gene encoding TcdB is located within a pathogenecity locus on the chromosome of *C. difficile* along with genes encoding TcdA (enterotoxin), TcdE, and regulators of toxin gene expression (TcdC and TcdR). While the sequence of TcdA, TcdE, TcdR, and TcdC are almost identical between historical and hypervirulent strains, TcdB is more variable (96% similarity, 92% identity). TcdB from a hypervirulent strain ($TcdB_{HV}$) has been found to be more potent on cultured cells than TcdB from a historical strain ($TcdB_{HIST}$). In line with this we also found that $TcdB_{HV}$ caused more extensive and broader tissue pathologies in a zebrafish embryo model. As a possible underlying mechanism for these differences in activity, it has been found previously that $TcdB_{HV}$ is translocated into cells more rapidly and is autoprocessed more efficiently than $TcdB_{HIST}$. Interestingly, the greatest sequence variation between the historical and hypervirulent strains of TcdB is found in the C-terminal domain (CTD), which is defined herein as the region of the toxin between amino acid 1651 and the terminal residue at position 2366. There is an overall 88% sequence identity between $TcdB_{HV}1651$-2366 and $TcdB_{HIST}1651$-2366. The CTD of TcdB encodes combined repetitive oligopeptides (CROPs), which are thought to be responsible for the recognition of glycans on target cells, and as such the CTD is often referred to as the receptor binding domain.

However, vaccination by targeting only secreted *C. difficile* toxins may run the risk of creating a pool of asymptomatic but infectious individuals, capable of transmitting toxigenic strains to others. For these reasons, vaccine researchers are also taking into consideration antigens that allow direct targeting of the pathogen. *C. difficile* expresses three major polysaccharide antigens known as polysaccharide I (PSI or PS-I), polysaccharide II (PSII or PS-II), and polysaccharide III (PSIII or PS-III) respectively. PSII is a poly-hexa-saccharide containing a repeating immunogenic phosphate moiety, and is expressed by all clinical *C. difficile* strains albeit in varying amounts. PSII intrinsically leads to T-independent humoral responses with poor B cell memory, but can be conjugated to protein carriers to induce antibody class switch and B cell memory. The PSII antigen therefore has proven immunogenicity and when conjugated to a protein carrier, induces a protective humoral immune response in animal models.

However, further improvement of the immunogenicity and protective response of vaccines against *C. difficile* is desired and it is to this goal that the novel compositions and vaccines of the present disclosure are directed.

BRIEF DESCRIPTION OF THE DRAWINGS

Several embodiments of the present disclosure are hereby illustrated in the appended drawings. It is to be noted however, that the appended drawings only illustrate several embodiments and are therefore not intended to be considered limiting of the scope of the present disclosure.

DETAILED DESCRIPTION

Figure 1:
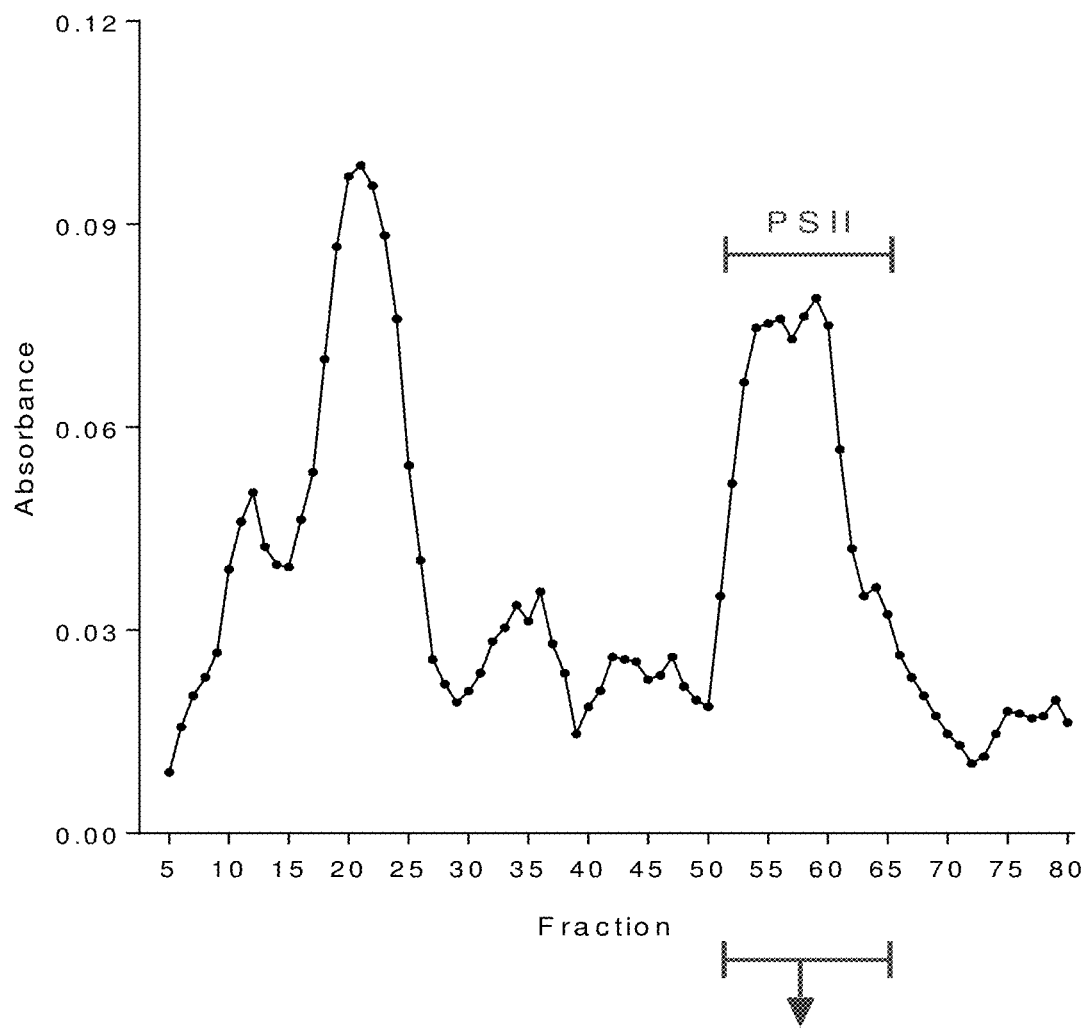
FIG. 1 shows a total carbohydrate profile of eluted fractions as determined by the sulfuric acid/phenol assay. A crude carbohydrate fraction was extracted from *C. difficile* using hot water and phenol. After dialysis, the crude carbohydrate preparation was applied to a GS50 size exclusion column. PSII was concentrated in the peak indicated. Data are representative of at least 4 experiments.

Seeking an improved *C. difficile* vaccine, we investigated using a combination of PSII and the glycolipid α-galactosylceramide (α-GC) as an immunogenic composition (vaccine) for providing enhanced protection against a live *C. difficile* challenge. PSII was isolated from a clinical *C. difficile* strain and was used to immunize B6 mice alone or with a PSII+α-GC combination. PSII-specific IgM and IgG3 titers were evident in sera from immunized mice, but the inclusion of α-GC led to an additional isotype switch and production of IgG1. Enhanced protection against *C. difficile* disease was therefore achieved by inclusion of the α-GC ligand and was associated with reduced bacterial numbers in fecal pellets. These results indicate that the α-GC stimulated a protective IgG1 response directed at the *C. difficile* PSII antigen. The present disclosure is thus directed to, in at least certain embodiments, a vaccine containing PSII and α-GC (or analogs or derivatives thereof) and optionally an adjuvant to provide protection targeted both at *C. difficile* toxins and the *C. difficile* pathogen. In alternative embodiments, the present disclosure is directed to immunogenic compositions which include PSII plus α-GC (or analogs or derivatives thereof), and all of or an immunogenic portion of the *C. difficile* secreted toxin B sequence known as C-terminal domain (CTD). The immunogenic compositions may further comprise an adjuvant, such an alum adjuvant (e.g., Alhydrogel®). The immunogenic composition may therefore comprise (1) PSII and α-GC±alum adjuvant, and/or (2) PSII, α-GC and CTD±alum adjuvant, in any combination of amounts that yields a safe and effective immune response against *C. difficile*.

In an alternate embodiment, α-GC and alum adjuvant (e.g., Alhydrogel®) can be used together in a prophylactic treatment for maintaining, enhancing, and/or protecting a subject's gut microflora. For example, the GC and alum adjuvant treatment can be given to a subject in advance of another procedure to be performed on the subject such as a surgery, immunotherapy, or antibiotic therapy, which could result in the depletion of or a challenge to the subject's gut microflora (i.e., microbiome).

Immunization with a PSII plus α-GC combination modality can be used in one embodiment as part of a prophylactic vaccine that not only protects against disease, but limits bacterial load, thereby reducing the risk of transmission to others. This vaccine method can also comprise a component of an immunization protocol whereby one or more of the secreted toxins TcdA and TcdB are targeted, thus limiting pathological effects of *C. difficile* as well as infection and bacterial burden.

Before further detailed description of various embodiments of the compositions and methods of use thereof of the present disclosure, it is to be understood that the present disclosure is not limited in application to the details of methods and compositions as set forth in the following description. The description provided herein is intended for purposes of illustration only and is not intended to be construed in a limiting sense. The present disclosure is capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that various embodiments of the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure as defined herein. Thus the examples described below, which include particular embodiments, will serve to illustrate the practice of the present disclosure, it being understood that the particulars shown are by way of example and for purposes of illustrative discussion of particular embodiments only and are presented in the cause of providing what is believed to be a useful and readily understood description of procedures as well as of the principles and conceptual aspects of the inventive concepts. Thus, while the compositions and methods of the present disclosure have been described in terms of particular embodiments, it will be apparent to those of skill in the art that variations may be applied to the compositions and/or methods and in the steps or in the sequence of steps of the method described herein without departing from the concept, spirit, and scope of the inventive concepts disclosed herein.

All patents, published patent applications, and non-patent publications mentioned in the specification are indicative of the level of skill of those skilled in the art to which the present disclosure pertains. Each patent, published patent application, and non-patent publication referenced in any portion of this application is expressly incorporated herein by reference in its entirety to the same extent as if the individual patent, or published patent application, or non-patent publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, observer error, and combinations thereof, for example. The term "about" or "approximately", where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 80% of the time, at least 90% of the time, at least 91% of the time, at least 92% of the time, at least 93% of the time, at least 94% of the time, at least 95% of the time, at least 96% of the time, at least 97% of the time, at least 98% of the time, or at least 99% of the time.

As used herein any reference to "one embodiment" or "an embodiment" means that a particular element, feature, composition, structure, or characteristic described in connection with the embodiment is included in at least one embodiment. The appearances of the phrase "in one embodiment" in various places in the specification are not necessarily all referring to the same embodiment.

The term "mutant" or "variant" is intended to refer to a protein, peptide, nucleic acid or organism which has at least one amino acid or nucleotide which is different from the wild type version of the protein, peptide, nucleic acid, or organism and includes, but is not limited to, point substitutions, multiple contiguous or non-contiguous substitutions, chimeras, or fusion proteins, and the nucleic acids which encode them. Examples of conservative amino acid substitutions include, but are not limited to, substitutions made within the same group such as within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, and valine), aromatic amino acids (such as phenylalanine, tryptophan, tyrosine) and small amino acids (such as glycine, alanine, serine, threonine, methionine). Other examples of possible substitutions are described below.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism without reference to how the active agent has its physiological effects.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The terms "subject" and "patient" are used interchangeably herein and will be understood to refer to a warm blooded animal, particularly a mammal. Non-limiting examples of animals within the scope and meaning of this term include dogs, cats, rabbits, rats, mice, guinea pigs, chinchillas, hamsters, ferrets, horses, pigs, goats, cattle, sheep, zoo animals, camels, llamas, non-human primates, including Old and New World monkeys and non-human primates (e.g., cynomolgus macaques, chimpanzees, rhesus monkeys, orangutans, and baboons), and humans.

Where used herein the term "active agent" refers to a compound or composition having biological activity.

"Treatment" refers to therapeutic treatments. "Prevention" refers to prophylactic or preventative treatment measures. The term "treating" refers to administering the composition to a patient for therapeutic purposes.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent which is sufficient to exhibit a detectable therapeutic effect without excessive adverse side effects (such as toxicity, irritation and allergic response) commensurate with a reasonable benefit/risk ratio when used in the manner of the inventive concepts. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition, disease or symptom thereof. A detectable or measurable improvement includes a subjective or objective decrease, reduction, inhibition, suppression, limit or control in the occurrence, frequency, severity, progression, or duration of the condition or disease, or an improvement in a symptom or an underlying cause or a consequence of the disease, or a reversal of the disease. A successful treatment outcome can lead to a "therapeutic effect," or "benefit" of ameliorating, decreasing, reducing, inhibiting, suppressing, limiting, controlling or preventing the occurrence, frequency, severity, progression, or duration of a disease or condition, or consequences of the disease or condition in a subject.

A decrease or reduction in worsening, such as stabilizing the condition or disease, is also a successful treatment outcome. A therapeutic benefit therefore need not be complete ablation or reversal of the disease or condition, or any one, most or all adverse symptoms, complications, consequences or underlying causes associated with the disease or condition. Thus, a satisfactory endpoint may be achieved when there is an incremental improvement such as a partial decrease, reduction, inhibition, suppression, limit, control, or prevention in the occurrence, frequency, severity, progression, or duration, or inhibition or reversal of the condition or disease (e.g., stabilizing), over a short or long duration of time (hours, days, weeks, months, etc.). Effectiveness of a method or use, such as a treatment that provides a potential therapeutic benefit or improvement of a condition or disease, can be ascertained by various methods and testing assays.

Where used herein, the term "*Clostridium difficile*" includes all strains of *C. difficile*, including, but not limited to, ribotype 027 (a.k.a. NAP1 and BI), VPI10463 strain (ribotype 003), ribotype W (a.k.a. NAP2), MOH 900 and MOH 718.

Where used herein, the term "vaccine" refers to a composition that prevents *C. difficile* infection, treats *C. difficile* infection, and/or reduces shedding of *C. difficile*.

Where used herein, the term α-galactosylceramide (α-GC) refers to the compound (2S,3S,4R)-1-O-(α-D-Galactosyl)-N-hexacosanoyl-2-amino-1,3,4-octadecanetriol, also known as "KRN700". Other α-GC analogs and derivatives which may be used in various embodiments described in the present disclosure include, but are not limited to, those shown in U.S. Pat. Nos. 5,936,076; 6,531,453; and 8,334, 408, and U.S. Patent Application Publications 20030157135; 20040242499; and 20120269857.

Where used herein, the term C-terminal domain (CTD) refers to amino acids 1651-2366 of the TcdB toxin protein, e.g., see U.S. Patent Application Publication 20160074496, or to any immunogenic portion thereof. Examples of TcdA and TcdB variants which may be used in certain embodiments of the immunogenic compositions described herein include those shown in U.S. Pat. No. 9,926,345.

Where used herein, the term "cross-neutralizing response" refers to an immune response which is at least partially effective against both a hypervirulent strain of *C. difficile* and a heterologous (historical) strain of *C. difficile*.

Where used herein, the term "eliciting an immune response" or "inducing an immune response" means initiating, triggering, causing, enhancing, improving or augmenting any response of the immune system, for example, of either a humoral or cell-mediated nature. The initiation or enhancement of an immune response can be assessed using assays known to those skilled in the art including, but not limited to, antibody assays (for example ELISA assays), antigen specific cytotoxicity assays and the production of cytokines (for example ELISPOT assays).

The term "derivative" as used herein means generally any structurally related molecule having the same scaffold as the basic molecule, but which is modified by the addition, deletion or substitution of one or more functional groups.

The term "peptide" is used herein to designate a series of amino acid residues, connected one to the other typically by peptide bonds between the alpha-amino and carbonyl groups of the adjacent amino acids to form an amino acid sequence. In certain embodiments, the peptides can range in length from 5 to 15 to 25 to 40 to 60 to 75 amino acids, for example, 5, 6, 7, 8, 9, 10, 11, 12, 13, 14, 15, 16, 17, 18, 19, 20, 21, 22, 23, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. The term "polypeptide" or "protein" is used herein to designate a series of amino acid residues, connected one to the other typically by peptide bonds between the alpha-amino and carbonyl groups of the adjacent amino acids, wherein the length is longer than a single peptide. A "fusion protein" or "fusion polypeptide" refers to proteins or polypeptides (and may be used interchangeably) which have been created by recombinant or synthetic methods to combine peptides in a serial configuration.

As used herein "immunogenic composition" refers to a composition containing, for example, peptides, polypeptides, fusion proteins, polysaccharides, glycoproteins, glycolipids, lipoproteins, or carrier molecules with such peptides, polypeptides, fusion proteins, polysaccharides, glycoproteins, glycolipids, and/or lipoproteins conjugated thereto, which elicits an immune response, such as the production of antibodies in a host cell, or host organism. The immunogenic composition may optionally contain an adjuvant. In certain embodiments, the immunogenic composition is a vaccine.

Where used herein, the term "antigenic fragment" refers to a fragment of an antigenic peptide or protein described herein which is also able to elicit an immunogenic response.

The term "homologous" or "% identity" as used herein means a nucleic acid (or fragment thereof) or an amino acid sequence (peptide or protein) having a degree of homology to the corresponding reference (e.g., wild type) nucleic acid, peptide or protein that may be equal to or greater than 70%, or equal to or greater than 80%, or equal to or greater than 85%, or equal to or greater than 86%, or equal to or greater than 87%, or equal to or greater than 88%, or equal to or greater than 89%, or equal to or greater than 90%, or equal to or greater than 91%, or equal to or greater than 92%, or equal to or greater than 93%, or equal to or greater than 94%, or equal to or greater than 95%, or equal to or greater than 96%, or equal to or greater than 97%, or equal to or greater than 98%, or equal to or greater than 99%. For example, in regard to peptides or polypeptides, the percentage of homology or identity as described herein is typically calculated as the percentage of amino acid residues found in the smaller of the two sequences which align with identical amino acid residues in the sequence being compared, when four gaps in a length of 100 amino acids may be introduced to assist in that alignment (as set forth by Dayhoff, in Atlas of Protein Sequence and Structure, Vol. 5, p. 124, National Biochemical Research Foundation, Washington, D.C. (1972)).

In one embodiment, the percentage homology as described above is calculated as the percentage of the components found in the smaller of the two sequences that may also be found in the larger of the two sequences (with the introduction of gaps), with a component being defined as a sequence of four, contiguous amino acids. Also included as substantially homologous is any protein product which may be isolated by virtue of cross-reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, Proc. Natl. Acad. Sci. USA 1990, 87, 2264-2268, modified as in Karlin & Altschul, Proc. Natl. Acad. Sci. USA 1993, 90, 5873-5877. In at least one embodiment "% identity" represents the number of amino acids or nucleotides which are identical at corresponding positions in two sequences of a protein having the same activity or encoding similar proteins. For example, two amino acid sequences each having 100 residues will have 95% identity when 95 of the amino acids at corresponding positions are the same. Similarly, two amino acid sequences each having 100 residues will have at least 90% identity when at least 90 of the amino acids at corresponding positions are the same. Similarly, two amino acid sequences each having 20 residues will have 95% identity when 19 of the amino acids at corresponding positions are the same, or 90% identity when at least 18 of the amino acids at corresponding positions are the same, or 85% identity when at least 17 of the amino acids at corresponding positions are the same, or 80% identity when at least 16 of the amino acids at corresponding positions are the same.

Further, where a sequence is described herein as having "at least X % identity to" a reference sequence, this is intended to include, unless indicated otherwise, all percentages greater than X %, such as for example, (X+1)%, (X+2)%, (X+3)%, (X+4)%, and so on, up to 100%.

Another example of a mathematical algorithm used for comparison of sequences is the algorithm of Myers & Miller, CABIOS 1988, 4, 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988, 85, 2444-2448.

Another algorithm is the WU-BLAST (Washington University BLAST) version 2.0 software (WU-BLAST version 2.0 executable programs for several UNIX platforms). This program is based on WU-BLAST version 1.4, which in turn is based on the public domain NCBI-BLAST version 1.4 (Altschul & Gish, 1996, Local alignment statistics, Doolittle ed., Methods in Enzymology 266, 460-480; Altschul et al., Journal of Molecular Biology 1990, 215, 403-410; Gish & States, Nature Genetics, 1993, 3: 266-272; Karlin & Altschul, 1993, Proc. Natl. Acad. Sci. USA 90, 5873-5877; all of which are incorporated by reference herein).

In addition to those otherwise mentioned herein, mention is made also of the programs BLAST, gapped BLAST, BLASTN, BLASTP, and PSI-BLAST, provided by the National Center for Biotechnology Information. These programs are widely used in the art for this purpose and can align homologous regions of two amino acid sequences. In all search programs in the suite, the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

The terms "polynucleotide sequence" or "nucleic acid," as used herein, include any polynucleotide sequence which encodes a peptide or fusion protein (or polypeptide) including polynucleotides in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand. The polynucleotide sequence encoding a peptide or fusion protein, or encoding a therapeutically-effective variant thereof can be substantially the same as the coding sequence of the endogenous coding sequence as long as it encodes an immunogenically-active peptide or fusion protein. Further, the peptide or fusion protein may be expressed using polynucleotide sequence(s) which differ in codon usage due to the degeneracies of the genetic code or allelic variations. Moreover, the peptides and fusion proteins of the present disclosure and the nucleic acids which encode them include peptide/protein and nucleic acid variants which comprise additional substitutions (conservative or non-conservative). For example, the immunogenic peptide variants include, but are not limited to, variants that are not exactly the same as the sequences disclosed herein, but which have, in addition to the substitutions explicitly described for various sequences listed herein, additional substitutions of amino acid residues (conservative or non-conservative) which substantially do not impair the activity or properties of the variants described herein. Examples of such conservative amino acid substitutions may include, but are not limited to, ala to gly, ser, or thr; arg to gln, his, or lys; asn to asp, gln, his, lys, ser, or thr; asp to asn or glu; cys to ser; gln to arg, asn, glu, his, lys, or met; glu to asp, gln, or lys; gly to pro or ala; his to arg, asn, gln, or tyr; ile to leu, met, or val; leu to ile, met, phe, or val; lys to arg, asn, gln, or glu; met to gln, ile, leu, or val; phe to leu, met, trp, or tyr; ser to ala, asn, met, or thr; thr to ala, asn, ser, or met; trp to phe or tyr; tyr to his, phe or trp; and val to ile, leu, or met.

The terms "infection," "transduction," and "transfection" are used interchangeably herein and mean introduction of a gene, nucleic acid, or polynucleotide sequence into cells such that the encoded protein product is expressed. The polynucleotides may comprise additional sequences, such as additional coding sequences within the same transcription unit, controlling elements such as promoters, ribosome binding sites, transcription terminators, polyadenylation sites, additional transcription units under control of the same or different promoters, sequences that permit cloning, expression, homologous recombination, and transformation of a host cell, and any such construct as may be desirable to provide embodiments of the present disclosure.

In certain embodiments, the present disclosure includes expression vectors capable of expressing one or more polypeptides. Expression vectors for different cell types are well known in the art and can be selected without undue experimentation. Generally, the DNA encoding the polypeptide is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Guidance can be found e.g., in Sambrook et al. Molecular Cloning: A Laboratory Manual, 3d ed., Cold Spring Harbor Laboratory Press, NY 2001)).

In certain embodiments, the present disclosure is directed to vaccine compositions useful in initiating an immune response against an organism of the genus *Clostridium* which comprise an immunogenic-effective amount of a toxin and/or a toxoid derived from the toxin of said organism in combination with a pharmaceutically acceptable carrier. In certain embodiments, the toxin is toxin B (TcdB), is derived from a hypervirulent strain of *C. difficile*, such as but not limited to hypervirulent strain ribotype 027, and is administered in the form of a toxoid formed from the toxin. The toxoid may be formed from the toxin in any appropriate manner known to persons having ordinary skill in the art. In at least one embodiment, the vaccine composition comprises a TcdB toxin or toxoid, wherein the TcdB toxin (or toxoid derived therefrom) is a natural toxin derived from a hypervirulent (HV) strain of *C. difficile*, such as the 027 ribotype or is a recombinantly-produced form of the toxin. In certain embodiments, the vaccine composition is effective against homologous and heterologous strains of *C. difficile*.

The present disclosure includes a method for stimulating an organism's immune response against *C. difficile*, the method comprising administering to said organism an effective amount of an immunogenic composition comprising of a PSII and α-GC or an α-GC analog or derivative thereof, optionally with a CTD or immunogenic portion thereof, and optionally with an alum adjuvant, in combination with a pharmaceutically acceptable carrier. The immune response may be a cross-neutralizing response. Routes of administration of the vaccine include, but are not limited to, parenteral, subcutaneous, intramuscular, intraperitoneal, and intravenous.

As noted, in certain embodiments, the present disclosure includes compositions which comprise an immunogenically-effective amount of a *C. difficile* PSII plus α-GC or an α-GC analog or derivative thereof, and optionally with a CTD or immunogenic portion thereof, and optionally with an alum adjuvant. Also as noted, the immunogenic compositions may further comprise one or more pharmaceutically-acceptable carriers, diluents, and/or adjuvants, such as physiological saline solutions, and buffered saline solutions at neutral pH such as phosphate buffered saline (PBS). Other types of carriers include liposomes or polymers and the like. The pharmaceutically acceptable carrier, diluent, or adjuvant can be selected by standard criteria. By "pharmaceutically acceptable" is meant a material that is not biologically or otherwise undesirable, i.e., the material may be administered to an individual along with the selected compound without causing any undesirable biological effects or interacting in an undesirable manner with any of the other components of the pharmaceutical composition in which it is contained. The carrier, diluent, or adjuvant may depend on the method of administration and the particular subject.

The immunogenic compositions described herein may be substantially pure, or combined with one or more immune-stimulating adjuvants. In certain embodiments, the immunogenic compositions comprise an alum (aluminum salt) adjuvant. Examples of alum-type adjuvants, which are usually provided as a hydrated gel, include but are not limited to, aluminum hydroxide (e.g. Alhydrogel®), aluminum phosphate (e.g., Adju-Phos®) aluminum hydroxyphosphate, aluminum sulfate, aluminum potassium sulfate, aluminum sodium sulfate, and aluminum ammonium sulfate. Other examples of adjuvants which may be used include, but are not limited to, Freund's incomplete adjuvant, Freund's Complete adjuvant, monophosphoryl lipid A, 1018 ISS, Ribi, Amplivax, AS15, BCG, CP-870,893, CpG7909, CyaA, Mologen's dSLIM, GM-CSF, IC30, IC31, Imiquimod, ImuFact IMP321, interferon-alpha or beta, IS Patch, ISS, ISCOMs, JuvImmune, LipoVac, MF59, and other non-toxic LPS derivatives, Montanide IMS 1312, Montanide ISA 206, Montanide ISA 50\1, Montanide ISA-51, OK-432, OM-174, nontoxic lipid A-related adjuvants such as, but not limited to, nontoxic monophosphoryllipid A (see, e.g., Persing et al., Trends Microbial. 10:s32-s37 (2002)), for example, 3 De-0-acylated monophosphoryllipid A (MPL) (see, e.g., United Kingdom Patent Application No. GB 2220211), silica, kaolin, muramyl dipeptide (MDP), lipopolysaccharide (LPS), carbon polynucleotides, i.e., poly IC and poly AU, QS21 and QuilA that comprise a triterpene glycoside or saponin isolated from the bark of the *Quillaja saponaria* Molina tree found in South America (see, e.g., Kensil et al., in Vaccine Design: The Subunit and Adjuvant Approach (eds. Powell and Newman, Plenum Press, NY, 1995); U.S. Pat. No. 5,057,540), polymeric or monomeric amino acids such as polyglutamic acid or polylysine, liposomes, and CpG (see, e.g., Klinman, Int. Rev. Immunol. 25(3-4):135-54 (2006); and U.S. Pat. No. 7,402,572. Other examples of adjuvants that may be used in the compositions disclosed herein include but are not limited to those disclosed in U.S. Pat. No. 8,895,514.

Optionally, the immunogenic composition can be combined with immunomodulators and immunostimulants (e.g., immune-stimulatory cytokines). The immunogenic composition may comprise microparticles such as liposomes or ISCOMs. The immunogenic compositions described herein may be substantially pure, or combined with one or more immune-stimulating adjuvants (as discussed elsewhere herein).

Generation of a protective immune response by the immunogenic composition can be measured by the development of antibodies. Non-limiting embodiments of therapeutically effective amounts of the active agent (active substance) of the immunogenic compositions that can form a protective immune response will generally contain sufficient active substance to deliver from about 0.01 µg/kg to about 100 mg/kg (weight of active substance/body weight of the subject). More particularly, the composition will deliver about 0.1 µg/kg to about 50 mg/kg, and more particularly about 1 µg/kg to about 10 mg/kg.

Dosage size may generally be determined in accordance with accepted practices in the art. The exact dosage for any given subject depends upon many factors, including the subject's size, general health, diet, sex, body surface area, age, the particular compound to be administered, time and route of administration, and other drugs being administered concurrently. Determination of optimal dosage is well within the abilities of a pharmacologist of ordinary skill. The therapeutically effective and non-toxic dose of the immunogenic composition can be determined by a person of ordinary skill in the art. Actual methods of preparing the appropriate dosage forms are known, or will be apparent, to those skilled in this art; for example, see Remington's Pharmaceutical Sciences, latest edition.

The immunogenic composition may be administered for example, only once, or at an interval of about 1 week to 6 weeks between immunizations. An immunogenic composition (i.e., vaccine) is administered in an amount sufficient to elicit production of antibodies as part of an immunogenic response. In certain embodiments, the immunogenic composition can be administered repeatedly with one to three month intervals between each dose and with an optional booster dose later in time. For example, after the first injection, a subject may receive one or more booster immunizations according to a particular (but non-limiting) schedule that may vary according to, inter alia, the immunogenic composition, adjuvants (if any) and/or the particular subject. Booster immunizations may be administered multiple times (e.g., two times or three times or four times or more), at desired time intervals ranging from, for example, about 2 weeks to about 26 weeks, such as 2, 4, 8, 12, 16, or 26 week intervals. The time intervals between different doses (e.g., between the primary dose and second dose, or between the second dose and a third dose) may not be the same, and the time interval between each two doses may be determined independently.

The immunogenic composition or the antibody produced therefrom can be administered post-infection or after a presumed infection, exposure or manifestation of clinical symptoms. For example, immunogenic composition or the antibody can be administered as a single dose or in multiple sequential doses, in a time period up to 8 hours post infection, 24 hours post infection, 48 hours post infection, 72 hours post infection, 4 days post infection, 5 days post infection, 6 days post infection, 7 days post infection, 10 days post infection, 2 weeks post infection, 3 weeks post infection, 4 weeks post infection, a month post infection, 2 months post infection, or later, post infection.

For prophylactic treatment against *C. difficile* infection, the immunogenic composition or the antibody produced therefrom can be administered prior to exposure of a subject to the bacteria so that the resulting immune response can inhibit or reduce the severity of the bacterial infection.

As explained, the immunogenic composition may comprise an antigenic fragment of a TcdB and/or TcdA toxoid, wherein such fragment is large enough to stimulate a protective immune response, including but not limited to a cross-neutralizing response. For example, the fragment may comprise a minimum length of 10, 25, 50, 75, 100, 125, 150, 175, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, or 2350 or more amino acids of the TcdB or TcdA toxoid. In one embodiment, the fragment is the CTD of the TcdB toxoid, or an immunogenic portion of the CTD.

The immunogenic compositions described herein are also useful as vaccines to generate neutralizing antibodies which can be used as a passive immune serum to treat or ameliorate the symptoms in patients. A vaccine composition as described above could be administered to an animal such as a horse, rabbit, or a human until a neutralizing antibody response is generated. These neutralizing antibodies can then be harvested, purified, and utilized to treat patients exhibiting symptoms in an amount effective to neutralize the effect of the pathogen. The neutralizing antibodies can be administered intravenously, intramuscularly, intradermally, subcutaneously, or any other appropriate manner known in the art. In one embodiment of the treatment method, the neutralizing antibody can be administered in conjunction with antibiotic therapy. The amount of neutralizing antibodies typically administered is about 1 mg of antibody to 1000 mg/kg, such as, for example, about 50-200 mg/kg of body weight.

The immunogenic compositions described herein may be formulated as sterile aqueous or non-aqueous solutions, suspensions or emulsions, which as described herein may additionally comprise a physiologically acceptable excipient (which may also be called carrier, vehicle, and/or a diluent). The immunogenic compositions may be in the form of a solid, liquid, or gas (aerosol). Alternatively, immunogenic compositions described herein may be formulated as a lyophilate (i.e., a lyophilized composition), or may be encapsulated within liposomes using technology well-known in the art.

The compositions and preparations described herein may be formulated for any appropriate manner of administration, including, for example, topical, buccal, lingual, oral, intranasal, intrathecal, rectal, vaginal, intraocular, subconjunctival, transdermal, sublingual or parenteral administration.

As noted elsewhere herein, the immunogenic compositions may also contain other components, which may be biologically active or inactive, including but not limited to, carbohydrates such as sugars and sugar alcohols, amino acids, peptides, and proteins. The sugars may be, for example, monosaccharides, disaccharides, or trisaccharides. These sugars may be used alone, as well as in combination with sugar alcohols. Examples of sugars include glucose, mannose, galactose, fructose or sorbose as monosaccharides, saccharose, lactose, maltose or trehalose as disaccharides and raffinose as a trisaccharide. A sugar alcohol may be, for example, mannitol and/or sorbitol. Examples of amino acids include glycine, arginine, and glutamic acid. An example of a protein is albumin. Furthermore, the compositions may include physiologically-well tolerated buffers (e.g., neutral buffered saline or phosphate buffered saline), antioxidants such as ascorbic acid or glutathione, preserving agents such as phenol, m-cresol, methyl- or propylparaben, chlorobutanol, thiomersal (thimerosal) or benzalkoniumchloride, and solubilizers such as polyethyleneglycols (PEG), e.g., PEG 3000, 3350, 4000 or 6000, or cyclodextrins, e.g., hydroxypropyl-cyclodextrin, sulfobutylethyl-cyclodextrin or y-cyclodextrin, or dextrans or poloxamers, e.g., poloxamer 407, poloxamer 188, Tween 20 or Tween 80, antioxidants, chelating agents such as EDTA, stabilizers, dyes, flavoring agents, and suspending agents and/or preservatives. In general, as discussed herein, the type of excipient is selected on the basis of the mode of administration.

In other embodiments, the present disclosure includes a kit comprising (a) a container that contains one or more pharmaceutical compositions as described herein, in solution or in lyophilized form; (b) optionally, a second container containing a diluent or reconstituting solution for the lyophilized formulation; and (c) optionally, instructions for (i) use of the solution or (ii) reconstitution and/or use of the lyophilized formulation. The kit optionally further comprises one or more of (iii) a buffer, (iv) a diluent, (v) a filter, (vi) a needle, or (v) a syringe. The container is (in a particular, non-limiting embodiment) a bottle, a vial, a syringe or test tube; and it may be a multi-use container. The container may be formed from a variety of materials such as glass or plastic. The kit and/or container may contain instructions on or associated with the container that indicates directions for reconstitution and/or use. For example, the label may indicate that the lyophilized formulation is to be reconstituted to amounts or concentrations of the active agent as described above. The label may further indicate that the formulation is useful or intended for subcutaneous or intramuscular administration, or other suitable method of administration. The container holding the formulation may be a multi-use vial, which allows for repeat administrations (e.g., from 2-6 administrations) of the reconstituted formulation. The kit may further comprise a second container comprising a suitable pharmaceutically-acceptable diluent, or other compound disclosed herein. The kit may further include other materials desirable from a commercial and user standpoint, including other excipients, buffers, diluents, filters, needles, syringes, and package inserts with instructions for use.

In animal subjects, the immune response may be monitored by periodically bleeding the animal, separating the sera from the collected blood, and analyzing the sera in an immunoassay, such as an ELISA assay, to determine the specific antibody titer. When an adequate antibody titer is established, the animal subject may be bled periodically to accumulate the polyclonal antisera. Polyclonal antibodies that bind specifically to the immunogen(s) may then be purified from immune antisera, for example, by affinity chromatography using protein A or protein G immobilized on a suitable solid support, as understood by persons having ordinary skill in the art. Affinity chromatography may be performed wherein an antibody specific for an Ig constant region of the particular immunized animal subject is immobilized on a suitable solid support. Affinity chromatography may also incorporate use of one or more immunogenic peptides, or fusion proteins, which may be useful for separating polyclonal antibodies by their binding activity to a particular immunogenic peptide. Monoclonal antibodies that specifically bind to an immunogenic peptide and/or fusion protein and immortal eukaryotic cell lines (e.g., hybridomas) that produce monoclonal antibodies having the desired binding specificity, may also be prepared, for example, using the technique of Kohler and Milstein ((Nature, 256:495-97 (1976), Eur. J. Immunol. 6:511-19 (1975)) and improvements thereto.

In certain embodiments, wherein the immunogenic composition comprises peptides, the peptides can either be concantenated (conjugated in series with or without linker sequences between the peptides to form one or more fusion polypeptides) or conjugated to one or more carrier molecules, as described in further detail below. Similarly, the active agents of the immunogenic composition may be conjugated or otherwise coupled to a suitable carrier molecule such as a protein. In various embodiments, the protein may be, but is not limited to, tetanus toxoid protein, diphtheria toxoid protein, CRM197 protein, MIEP (major immunoenhancing protein) from *Neisseria meningitidis* outer membrane complex, *Haemophilus influenzae* protein D, pertussis toxin mutant, *Bordetella pertussis* fimbriae, keyhole limpet haemocyanin (KLH), ovalbumin, bovine serum albumin (BSA), cholera toxoid (CT), recombinant *Pseudomonas aeruginosa* exotoxin A (rEPA), and *C. difficile* toxins A (TcdA) and B (TcdB). The carrier molecule may be attached to the cell surface polysaccharide using known methods. For example, via an ester or amide linkage between available hydroxy or carboxy groups on the saccharides and carboxyl or amine groups on the protein. Other examples of carrier proteins which may be used include, but are not limited to, those disclosed in U.S. Pat. No. 4,673,574 and U.S. Published Patent Applications 2013/0072881, 2013/0209503, and 2013/0337006. The carrier may be a surface such as a microarray.

The active agents may be attached to the carrier molecule using known methods, such as but not limited to an ester or amide linkage between available hydroxy or carboxy groups on the saccharides and carboxyl or amine groups on the protein. In certain embodiments the active agents are linked to the carrier via a linker or spacer molecule ("linker"). The linker may be an aliphatic or aromatic residue, e.g. an alkyl(en) group or phenyl(en) group, comprising a reactive functional group, such as an amino group, preferably a primary amino group, (activated) carboxy group, aldehyde, azide, alkenyl or alkinyl group. The linker may comprise a polyether or polyester chain. The linker may be selected from the group comprising primary alkylamines, alkyl, aryl, alkylaryl, and aralkyl residues with a terminal aldehyde, azide, alkine or alkene group or (activated) carboxy group, and residues comprising a reactive amine, aldehyde or azide group, or (activated) carboxy group.

As noted above, the immunogenic compositions of the present disclosure can be administered by any suitable manner known in the art, e.g., orally, intramuscularly, intravenously, sublingual, mucosal, intraarterially, intrathecally, intradermally, intraperitoneally, intranasally, intrapulmonarily, intraocularly, intravaginally, intrarectally, or subcutaneously. They can be introduced into the gastrointestinal tract or the respiratory tract, e.g., by inhalation of a solution or powder containing the conjugates. In some embodiments, the compositions can be administered via absorption via a skin patch. Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained.

Several embodiments of the present disclosure will now be discussed in terms of several specific, non-limiting, examples. The examples described below will serve to illustrate the practice of the present disclosure, it being understood that the particulars shown are by way of example and for purposes of illustrative discussion of particular embodiments of the present disclosure only and are presented in the cause of providing what is believed to be a useful and readily understood description of procedures as well as of the principles and conceptual aspects of the inventive concepts.

Experimental Methods

Mice: Female C57Bl/6 (B6) mice were purchased from Charles River (Bethesda, Md., USA). Heterozygous Traj18$^{+/-}$ mice were purchased from Jax.org and bred to generate Traj18$^{-/-}$, Traj18$^{+/-}$, and Traj18$^{+/+}$ offspring. Experiments were conducted on mice that were both littermates and cage mates. Genotyping and phenotyping was performed according to protocols provided by Jax.org.

Reagents: α-GC was purchased from Axorra LLC (Farmingdale, N.Y.). HRP-conjugated Abs for ELISA were purchased from Southern Biotech (Birmingham, Ala.).

PSII Purification: PSII was prepared by the method described by Monteiro (Monteiro, M. A. 2016. The Design of a *Clostridium difficile* Carbohydrate-Based Vaccine. *Methods Mol Biol* 1403: 397-408). In brief, a wet paste of *C. difficile* (strain VPI10463) was subject to phenol/hot water extraction. After dialysis of the partitioned aqueous phase, carbohydrate-enriched material was freeze dried under vacuum and then re-constituted in ddH$_2$O. Samples were run on a Sephadex G25 gravity column and fractions were analyzed by 31P NMR (Oklahoma State University NMR Facility, Stillwater, Okla.). Nucleic acids and proteins could not be detected in the PSII-containing fractions.

Immunizations: Mice were immunized s.c. in both flanks with a total of 15 μg or 50 μg PSII or PSII plus 4 μg α-GC, in a 200 μl total volume of sterile low-endotoxin PBS. The amount of α-GC administered has been determined in previous studies to exert a strong CD1d- and NKT-dependent effect on Ab responses. The booster vaccine comprised 7.5 μg PSII in PBS administered s.c. over both flanks. The booster was administered 1 week after the primary immunization.

*C. difficile* spore preparation: *C. difficile* spores were streaked onto a TCCFA (Taurocholate Cycloserine Cefoxitin Fructose Agar) plate to generate single colonies which were isolated and cultured in Columbia broth overnight. The strains were then grown in Clospore media. All the experiments were done under anaerobic conditions at 37° C. Spores were harvested by repeated centrifugation of the culture stock (3200 rpm for 20 min at 4° C.) until the supernatants were clear. Pellets were re-suspended in ice-cold water.

Challenge Assays: Mice were given 0.5 mg/ml Cefoperazone in drinking water for 10 days. Sterile drinking water was then provided for a further 2 days. The mice were then challenged by oral gavage with a 20 μl inoculum of water containing 1-2×10$^4$ VPI 10463 spores. Animal weight was then measured daily.

Quantification of fecal *C. difficile* CFU: Fecal samples were prepared by homogenizing pellets with 1×PBS. Serial dilutions were made for each sample using sterile 1× PBS before being plated on TCCFA under anaerobic conditions at 37° C. The plates were incubated for 48 hours and *C. difficile* colonies, which appear as flat, smeared and irregular, were counted. The detection limit for this assay is 100 Colony-forming units.

ELISA: Assays were performed as described by Devera et al (Devera, T. S., H. B. Shah, G. A. Lang, and M. L. Lang. 2008. Glycolipid-activated NKT cells support the induction of persistent plasma cell responses and antibody titers. *European journal of immunology* 38: 1001-1011) with PSII being used to coat the plates (10 μg/ml final concentration in TBS buffer).

Statistics: Data were analyzed using GraphPad Prism 6.0 (La Jolla, Calif., USA). A two-tailed Mann-Whitney U-test and an ANOVA with Dunn's post-test were used to compare two and multiple experimental groups respectively.

Treatment Method Summary:
Step 1: Female B6 mice at age 6 weeks were immunized s.c. in each flank on day 0 with 100 µl volumes of the following sham treatments or vaccines: sterile PBS vehicle (FIG. 6a, b, d); 15 µg PSII (FIG. 6c); 4 µg α-GC (FIGS. 6e, g), and 15 µg PSII plus 4 µg α-GC (FIG. 6f).
Step 2: On day 7, groups of FIGS. 6c, d, e, and f received a booster vaccine comprising 7.5 µg PSII, while the group of FIG. 6g received a booster comprising vehicle.
Step 3: Mice were treated for 10 days with the antibiotic cefoperazone ad libitum in drinking water (0.5 µg/ml).
Step 4: Antibiotic was withdrawn for 2 days before oral gavage with sterile water (FIG. 6a) or $10^4$ CFU C. difficile VPI10463 spores (FIG. 6b-g).
Step 5: Weights were measured daily. Fecal pellets were collected for analyses. Pellets from 3 days after gavage were used for enumeration of bacteria. Using a standard method, C. difficile-associated colony forming units were measured. (FIG. 6h).

Results

Enrichment of PSII for Immunization Studies

Figure 2:
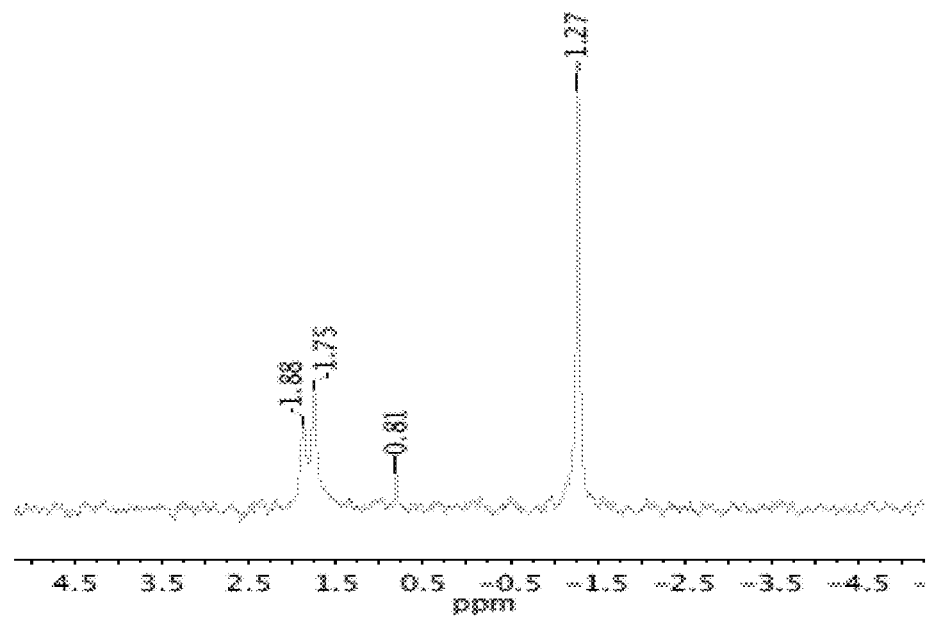
FIG. 2 shows results of a 31P NMR analysis on the PSII fraction from the analysis of FIG. 1. Analysis confirmed the predominance of PSII in the column fractions.
Figure 3:
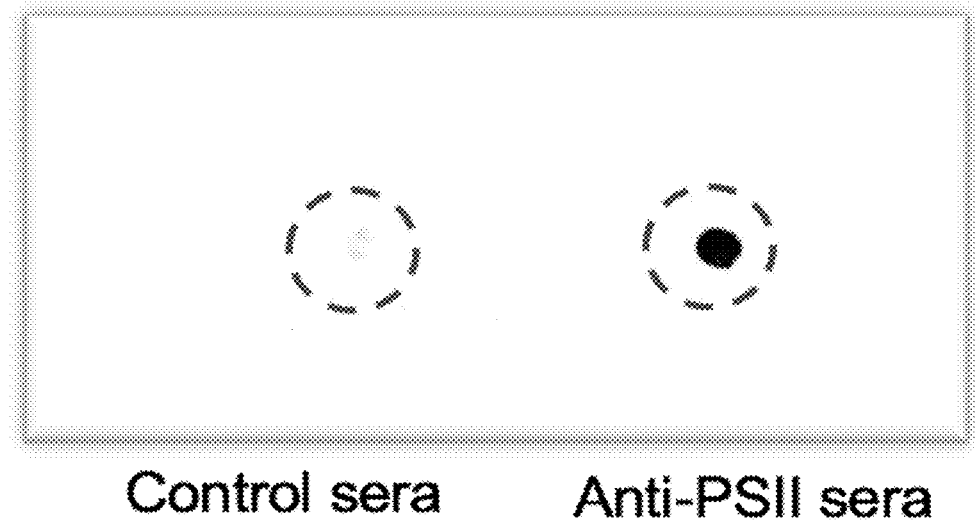
FIG. 3 shows that a rabbit anti-PSII but not a control anti-sera were able to detect PSII by dot blot. Neither proteins nor nucleic acids could be detected in the column fractions where PSII was concentrated.

All clinical strains of C. difficile express PSII, a polyhexa-saccharide containing a repeating immunogenic phosphate moiety, which can stimulate protective Ab responses when conjugated to a T-dependent protein carrier. As noted above, here we used a modified version of the method by Monteiro and colleagues to isolate PSII. A C. difficile-derived phenol/hot water-extracted crude carbohydrate preparation was applied to a Sephadex size exclusion gravity column (FIG. 1). This resulted in elution of two major peaks from fractions 5-30 and 50-75, with the former consisting largely of PSIII, nucleic acids, and proteins. The latter peak did not contain detectable protein or nucleic acid and a 31P NMR analysis revealed three major peaks, with the most abundant (at −1.27 ppm) representing PSII (FIG. 2). The less abundant peaks at 1.88 ppm and 1.75 ppm represent PSIII. Further resolution of the PSII/PSIII peak was possible by pooling fractions into four batches and by selecting the highest fraction numbers. PSII-specific antisera and naïve control antisera were used to probe the PSII-enriched fractions by dot blot (FIG. 3) which revealed that the fraction comprised PSII. Anti-sera were a gift from Dr. Gayatri Vedantam at Arizona State University; work using these was published in PloSPathog., 2016 Oct. 14; 12(10):e1005946. An ELISA assay in which plates were coated with purified PSII was also optimized for this work. Anti-PSII but not control anti-sera detected the isolated PSII. The PSII isolated was used as the immunogen for the studies described herein.

Figure 4:
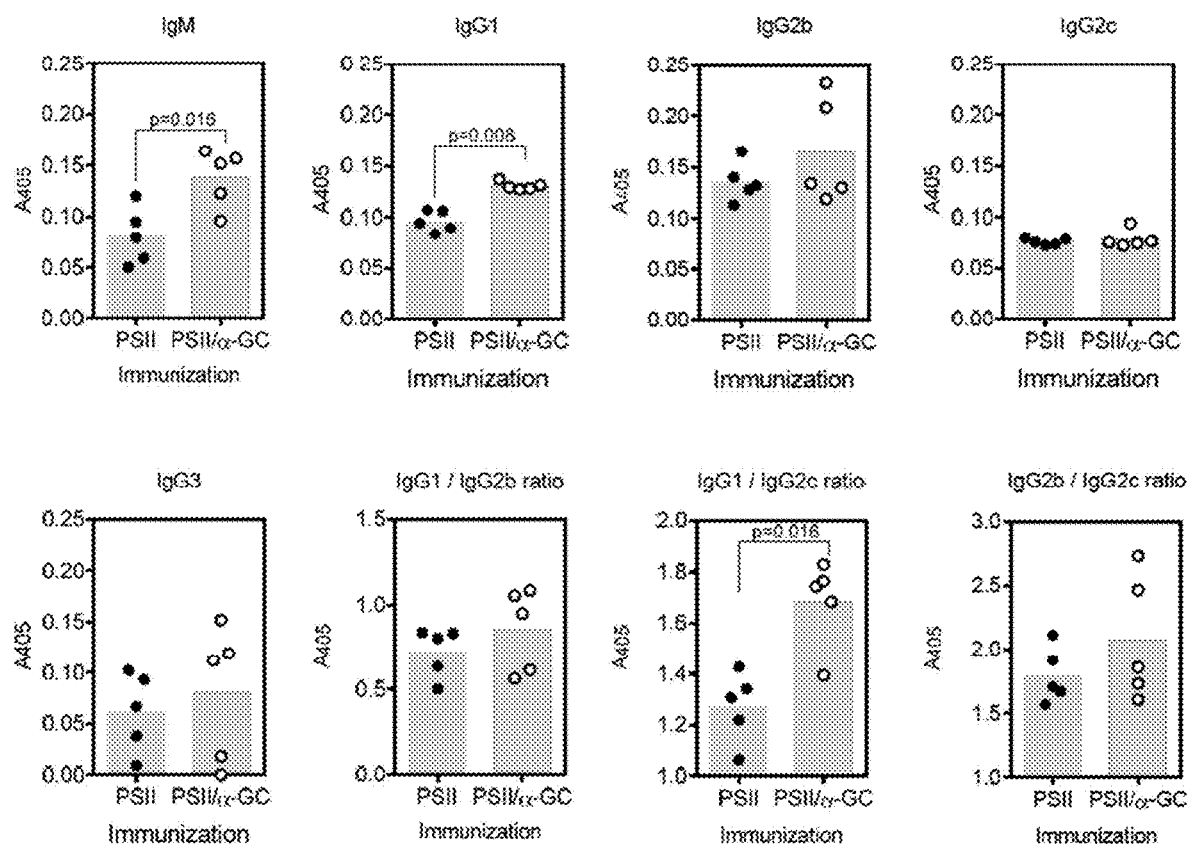
FIG. 4 shows results after B6 mice were immunized subcutaneously (s.c.) with 15 μg PSII or PSII plus 4 μg α-galactosylceramide (α-GC). After one week, mice were boosted with 7.5 μg PSII. Sera were collected after 28 days and PSII-specific IgM, IgG1, the IgG2 isotypes IgG2b and IgG2c, and IgG3 detected by ELISA. Sera from mice treated with the PSII/α-GC combination demonstrated an IgG1 class switch. Each data point represents an individual mouse. A student's t-test was used to detect significant differences between groups.
Figure 5:
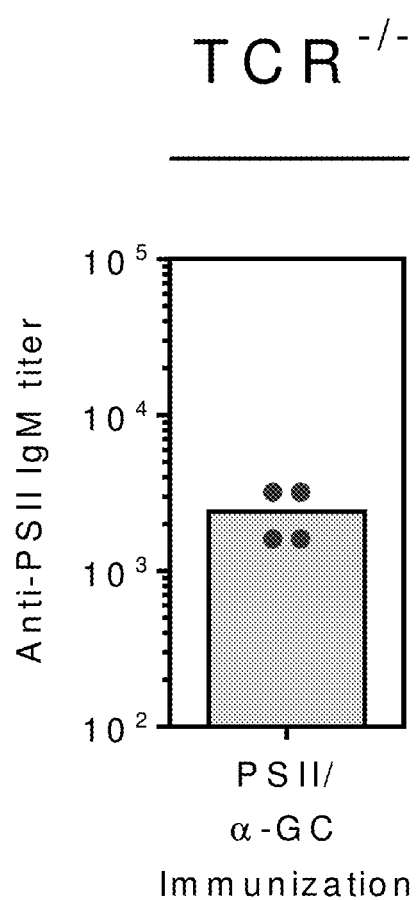
FIG. 5 shows IgM detected by ELISA in TCR$^{-/-}$ mice immunized with the PSII/α-GC combination.

Antibody Response to PSII is Altered by an NKT Cell-Activating Glycolipid Adjuvant B6 mice were immunized with PSII alone or PSII plus α-GC. In response to PSII alone, PSII-specific IgM and IgG3 were produced and there was no detectable IgG (FIG. 4). Inclusion of α-GC in the vaccine did not significantly alter IgM or IgG3 production, but did induce production of PSII-specific IgG1. TCRα$^{-/-}$ mice, lacking classical αβ T cells and NKT cells, were immunized with PSII plus α-GC and only IgM production was detected (FIG. 5). These results show that PSII stimulates a classical T-independent Ab profile.

B6 mice were immunized with PSII alone or PSII plus the CD1d-binding glycolipid adjuvant α-GC. In response to PSII alone, PSII-specific IgM and IgG3 were produced and there was low but detectable IgG1 (FIG. 4). Inclusion of α-GC in the vaccine did not significantly alter IgM or IgG3 production, but did increase production of PSII-specific IgG1. Low amounts of the IgG2 isotypes (IgG2b and IgG2c) were detected and unchanged by α-GC inclusion. Furthermore, the IgG1/IgG2c ratio, reflective of the T helper 1/T helper 2 balance in the immune response was increased FIG. 4). TCRα$^{-/-}$ mice, lacking classical αβ T cells and NKT cells, were also immunized with PSII plus α-GC and only IgM production was detected (FIG. 5). These results show that PSII stimulates a classical T-independent Ab profile, which can be altered by NKT-activating glycolipid adjuvant. This indicates that NKT cells provide specific B cell help that drives IgG1 isotype switch against the PSII Ag. Anti-PSII titers could not be detected in mice immunized with α-GC alone.

PSII Vaccine-Induced Protection Against C. Difficile is Enhanced by α-GC

Figure 6:
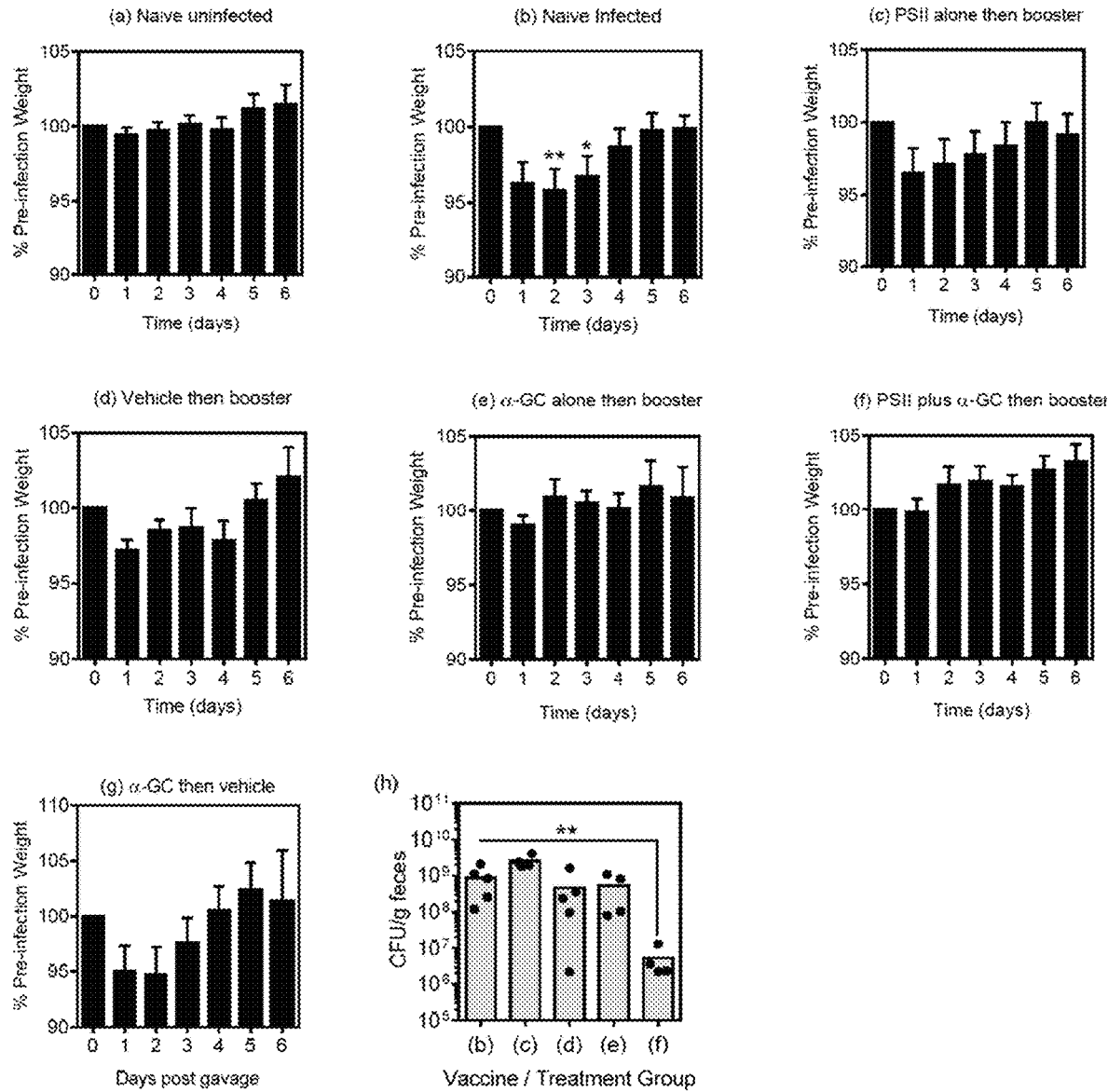
FIG. 6 shows that vaccination with PSII and α-GC leads to enhanced protection against *C. difficile* disease when measured against weight loss. Non-immunized age- and sex-matched naïve B6 mice were Cefoperazone-treated and then treated with vehicle only (a) or were infected with $10^4$ live *C. difficile* spores (b). Some mice were administered PSII alone followed by a PSII booster one week later (c), or administered vehicle only followed by the PSII booster one week later (d), or administered α-GC alone followed by the PSII booster (e), or administered a PSII and α-GC combination followed by the PSII booster (f), or administered α-GC alone followed by vehicle (g). Animals were then treated with the antibiotic Cefoperazone prior to being infected with $10^4$ live *C. difficile* spores. Graphs show the percent of original weight, which was obtained daily and for the duration indicated. Graphs show the percent of original weight, which was obtained daily and for the duration indicated. Five mice were used for each group except for the naïve-infected and the PSII/α-GC groups (n=10). Fecal pellets were collected 2 days after infection in the b, c, d, e, and f treatment groups. Fecal *C. difficile* bacterial loads are shown (h). In the uninfected control group (a), zero counts were detected (limit of detection in assay=$10^2$).

FIGS. 6(a-h) show results of C. difficile-infected mice treated with various potentially immunogenic test compositions. Naïve B6 mice were pre-treated for 10 days with Cefoperazone followed by oral gavage with water (naïve uninfected—FIG. 6a) or with water containing $10^4$ C. difficile VPI 10463 spores (naïve infected—FIG. 6b). The uninfected mice made marginal weight gains over the 6 day follow-up period, demonstrating that the gavage method had no adverse effects related to eating or drinking (FIG. 6a). In contrast the naïve infected mice demonstrated a small (5-10%) but significant loss in total body weight that took 5 additional days to return to the pre-infection state (FIG. 6b). B6 mice were also immunized prior to Cefoperazone treatment and oral gavage (FIG. 6c-g). Mice that were given PSII alone, followed by a PSII booster (FIG. 6c), or given just the booster, w/o initial PSII (FIG. 6d), demonstrated a similar pattern to that of naïve infected mice, suggesting that PSII alone did not lead to protection. When mice were treated with α-GC to activate NKT cells and followed one week later with PSII, no weight loss was observed (FIG. 6e). When mice were immunized with PSII plus α-GC and followed by the PSII booster, no weight loss occurred (FIG. 6f). A marginal, non-significant weight gain was observed similar to that of the naïve uninfected group. Immunization with α-GC alone (w/o a PSII booster) did not protect against weight loss (FIG. 6g). These data demonstrate that inclusion of α-GC in the PSII vaccine leads to enhanced protection upon challenge with live C. difficile spores, while α-GC alone did not lead to protection. FIG. 6h shows C. difficile bacterial load in fecal pellets collected from several treatment groups two days after infection with live C. difficile spores. Mice immunized with PSII plus α-GC and followed by the PSII booster showed a significant reduction in fecal C. difficile bacterial load as compared to other treatments.

NKT Cell-Dependency of the α-GC Adjuvant Effect

Figure 7:
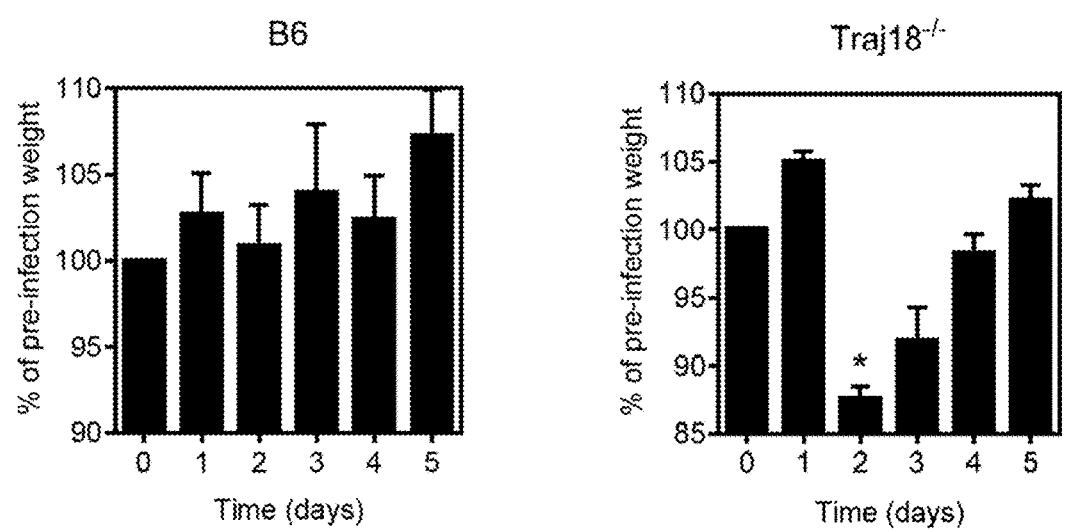
FIG. 7 shows NKT cells are required for the adjuvant effect of α-GC on protection against *C. difficile*. Mice depicted were immunized with PSII plus α-GC before treating with Cefoperazone and infecting with *C. difficile*. Results are shown for control B6 mice (lefthand panel) and NKT-deficient Traj18$^{-/-}$ mice (righthand panel). Data shows mean weight. 5 mice were used for each group.
Figure 8:
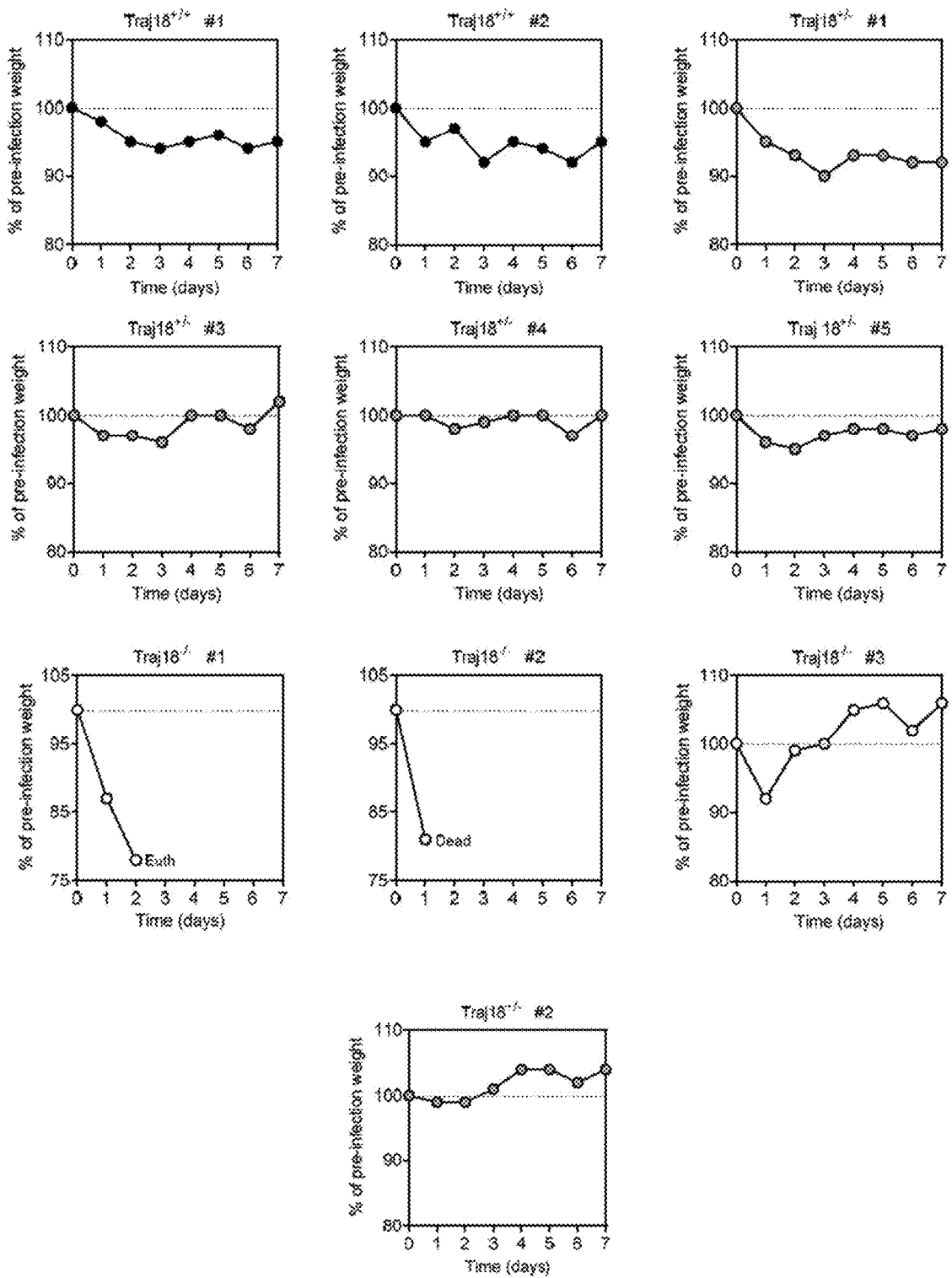
FIG. 8 shows results for Traj18$^{+/+}$, Traj18$^{+/-}$, and Traj18$^{-/-}$ littermates (and cage mates) immunized with PSII plus α-GC before treating with Cefoperazone and infecting with *C. difficile* as described. Each graph depicts weight loss and recovery or euthanasia in an individual mouse.

To confirm NKT cell dependence of the protective response, mice Traj18$^{-/-}$ mice lacking α-GC-reactive NKT cells, were also immunized before antibiotic treatment and infection with $3\times10^4$ spores per animal. All B6 mice were protected against weight loss (FIG. 7, left panel), whereas all Traj18$^{-/-}$ mice lost at least 10% of overall body weight before recovery by day 5 post-infection FIG. 7, right panel). This demonstrated that NKT cells were required for the response to the PSII/α-GC combination and consistent with results in B6 mice whereby PSII alone was not protective. In a follow up experiment, heterozygous Traj18$^{+/-}$ mice were bred to generate littermates that had the Traj18$^{+/+}$, Traj18$^{+/-}$, and Traj18$^{-/-}$ genotypes respectively. The mice were then immunized with PSII/α-GC, antibiotic-treated and challenged with a larger dose of *C. difficile* spores (10⁵ per mouse) (FIG. 8). It was observed that the NKT-sufficient Traj18⁺/⁺ and Traj18+/− mice demonstrated resistance to weight loss, whereas the Traj18⁻/⁻ mice were more susceptible. Of the Traj18⁻/⁻ mice, ⅔ died or were euthanized due to extreme weight loss (>20%) and ⅓ lost 8% of body weight and recovered. These results show that NKT cells were required for protection induced by the PSII/α-GC vaccination modality.

In at least certain embodiments, the present disclosure is directed to an immunogenic composition, comprising a *Clostridium difficile* (*C. difficile*) surface polysaccharide II (PSII) or an immunogenic portion thereof; and an α-galactosylceramide (α-GC) or analog or derivative thereof, which is able to bind to a CD1d glycoprotein. The immunogenic composition may further comprise a *C. difficile* TcdA and/or TcdB toxin or toxoid, or an immunogenic portion thereof. The TcdB toxin, toxoid, or immunogenic portion thereof may be from a hypervirulent strain of *C. difficile*. The hypervirulent strain may be ribotype 027. The immunogenic composition may further comprise a *C. difficile* TcdB C-terminal domain (CTD), or an immunogenic portion thereof. The CTD or immunogenic portion thereof may be from a hypervirulent strain of *C. difficile*, which may be ribotype 027. Any of the mentioned compositions may further comprise an adjuvant such as alum, and/or a pharmaceutically-acceptable excipient.

In at least certain embodiments, the present disclosure is directed to a method of treating, ameliorating, or inhibiting a *C. difficile* infection or a *C. difficile*-associated diarrhea in a subject in need of such treatment, comprising administering to the subject an effect amount of an immunogenic composition comprising a *Clostridium difficile* (*C. difficile*) surface PSII or an immunogenic portion thereof; and an α-GC or analog or derivative thereof, which is able to bind to a CD1d glycoprotein. The immunogenic composition may further comprise a *C. difficile* TcdA and/or TcdB toxin or toxoid, or an immunogenic portion thereof. The TcdB toxin, toxoid, or immunogenic portion thereof may be from a hypervirulent strain of *C. difficile*. The hypervirulent strain may be ribotype 027. The immunogenic composition may further comprise a *C. difficile* TcdB C-terminal domain (CTD), or an immunogenic portion thereof. The CTD or immunogenic portion thereof may be from a hypervirulent strain of *C. difficile*, which may be ribotype 027. Any of the mentioned compositions may further comprise an adjuvant such as alum, and/or a pharmaceutically-acceptable excipient. The subject in need of the treatment may be a patient in a population at risk for a *C. difficile* infection, including but not limited to workers and patients in healthcare, nursing home, assisted-living, or retirement facilities, candidates for surgical procedures, recipients of extended antibiotic or steroid treatment, patients having celiac disease, autoimmune diseases, AIDS, and/or inflammatory bowel disease, or patients who are immunesuppressed. The treatment method may result in at least a 100-fold decrease in *C. difficile* fecal load as compared to a subject not treated with α-GC.

In at least certain other embodiments, the present disclosure is directed to a method of treating a subject to protect the subject's gut microflora, comprising administering to the subject an effective amount of a composition comprising (a) a *Clostridium difficile* (*C. difficile*) surface PSII or an immunogenic portion thereof, and an α-GC or analog or derivative thereof, which is able to bind to a CD1d glycoprotein; or (b) an α-GC or analog or derivative thereof, which is able to bind to a CD1d glycoprotein; and an alum adjuvant. The composition may further comprise a *C. difficile* TcdA and/or TcdB toxin or toxoid, or an immunogenic portion thereof. The immunogenic portion may further comprise a *C. difficile* TcdB C-terminal domain (CTD), or an immunogenic portion thereof. The treatment may be provided prior to a surgery, immunotherapy, antibiotic therapy, or *C. difficile* treatment performed on the subject.

It will be understood from the foregoing description that various modifications and changes may be made in the various embodiments of the present disclosure without departing from their true spirit. The description provided herein is intended for purposes of illustration only and is not intended to be construed in a limiting sense. Thus, while embodiments of the present disclosure have been described herein so that aspects thereof may be more fully understood and appreciated, it is not intended that the present disclosure be limited to these particular embodiments. On the contrary, it is intended that all alternatives, modifications and equivalents are included within the scope of the inventive concepts as defined herein. Thus the examples described above, which include particular embodiments, will serve to illustrate the practice of the present disclosure by way of example and for illustrative purposes. Changes may be made in the formulations and compositions described herein, the methods described herein or in the steps or the sequence of steps of the methods described herein, without departing from the spirit and scope of the present disclosure.

What is claimed is:

1. An immunogenic composition, comprising:
   a *Clostridium difficile* (*C. difficile*) surface polysaccharide II (PSII) or an immunogenic portion thereof;
   an immunogen selected from the group consisting of (i) a *C. difficile* TcdA toxin, toxoid, or immunogenic portion thereof, (ii) a TcdB toxin, toxoid, or immunogenic portion thereof, and (iii) a TcdB C-terminal domain (CTD) or immunogenic portion thereof; and
   an α-galactosylceramide (α-GC) or derivative thereof, which is able to bind to a CD1d glycoprotein.

2. The immunogenic composition of claim 1, wherein the TcdB toxin, toxoid, or immunogenic portion thereof is from a hypervirulent strain of *C. difficile*.

3. The immunogenic composition of claim 2, wherein the hypervirulent strain is ribotype 027.

4. The immunogenic composition of claim 1, wherein the CTD or immunogenic portion thereof is from a hypervirulent strain of *C. difficile*.

5. The immunogenic composition of claim 4, wherein the hypervirulent strain is ribotype 027.

6. The immunogenic composition of claim 1, further comprising an alum adjuvant.

7. The immunogenic composition of claim 1, further comprising a pharmaceutically-acceptable excipient.

8. A method of treating, ameliorating, or inhibiting a *C. difficile* infection or a *C. difficile*-associated diarrhea in a subject in need of such treatment, comprising:
   administering to the subject an effect amount of an immunogenic composition, comprising: a *Clostridium difficile* (*C. difficile*) surface polysaccharide II (PSII) or an immunogenic portion thereof; an immunogen selected from the group consisting of (i) a *C. difficile* TcdA toxin, toxoids immunogenic portion thereof, (ii) a TcdB toxin, toxoid, or immunogenic portion thereof, and (iii) a TcdB C-terminal domain (CTD) or immunogenic portion thereof; and an α-galactosylceramide (α-GC) or derivative thereof, which is able to bind to a CD1d glycoprotein.

9. The method of claim 8, wherein the subject in need of the treatment is a patient in a population at risk for a *C. difficile* infection, the population comprising workers and patients in healthcare, nursing home, assisted-living, or retirement facilities, candidates for surgical procedures, recipients of extended antibiotic or steroid treatment, patients having celiac disease, autoimmune diseases, AIDS, and/or inflammatory bowel disease, or who are immunesuppressed.

10. The method of claim 8, wherein the treatment results in a 100-fold decrease in *C. difficile* fecal load as compared to a subject not treated with α-GC.

11. A method of treating a subject to protect the subject's gut microflora, comprising:
   administering to the subject an effective amount of a composition comprising:
   (a) a *Clostridium difficile* (*C. difficile*) surface polysaccharide II (PSII) or an immunogenic portion thereof; an immunogen selected from the group consisting of (i) a *C. difficile* TcdA toxin, toxoid, or immunogenic portion thereof, (ii) a TcdB toxin, toxoid, or immunogenic portion thereof, and (iii) a TcdB C-terminal domain (CTD) or immunogenic portion thereof; and an α-galactosylceramide (α-GC) or derivative thereof, which is able to bind to a CD1d glycoprotein.

12. The method of claim 11, wherein the treatment is provided prior to a surgery, immunotherapy, or antibiotic therapy on the subject.

\* \* \* \* \*